United States Patent
Ho et al.

(10) Patent No.: US 12,005,091 B2
(45) Date of Patent: Jun. 11, 2024

(54) USE OF LACTIC ACID BACTERIA OR FERMENTATION PRODUCT THEREOF FOR MAINTAINING OR IMPROVING GASTROINTESTINAL CONDITION

(71) Applicant: GLAC BIOTECH CO., LTD, Tainan (TW)

(72) Inventors: Hsieh-Hsun Ho, Tainan (TW); Wen-Yang Lin, Tainan (TW); Jui-Fen Chen, Tainan (TW); Yi-Wei Kuo, Tainan (TW); Jia-Hung Lin, Tainan (TW); Chi-Huei Lin, Tainan (TW); Ching-Wei Chen, Tainan (TW); Yu-Fen Huang, Tainan (TW)

(73) Assignee: GLAC BIOTECH CO., LTD, Tainan (TW)

(*) Notice: Subject to any disclaimer, the term of this patent is extended or adjusted under 35 U.S.C. 154(b) by 55 days.

(21) Appl. No.: 17/726,843

(22) Filed: Apr. 22, 2022

(65) Prior Publication Data

US 2023/0310523 A1    Oct. 5, 2023

(30) Foreign Application Priority Data

Mar. 29, 2022  (TW) ................... 111112005

(51) Int. Cl.
*A61K 35/747* (2015.01)
*A61P 31/04* (2006.01)

(52) U.S. Cl.
CPC ............ *A61K 35/747* (2013.01); *A61P 31/04* (2018.01)

(58) Field of Classification Search
CPC .............................. A61K 35/747; A61P 31/04
See application file for complete search history.

(56) References Cited

U.S. PATENT DOCUMENTS

2010/0166721 A1* 7/2010 Masri ............... A61K 35/74
424/93.44

FOREIGN PATENT DOCUMENTS

CN        113082149 A  *  7/2021  ........... A61K 36/896

OTHER PUBLICATIONS

Mirjana Rajilić-Stojanović et al., The first 1000 cultured species of the human gastrointestinal microbiota, FEMS Microbiol Rev. Sep. 2014; 38(5): 996-1047 (Year: 2014).*
CN113082149A, Google English Translation, downloaded in Aug. 2023 (Year: 2023).*
Chiao-Wen Lin et al, Lozenges with probiotic strains enhance oral immune response and health, Oral Diseases, vol. 28, Issue 6, Sep. 2022, First published date: Mar. 22, 2021 (Year: 2021).*
Sarah E. Blutt et al, The gastrointestinal frontier: IgA and viruses, Frontiers in Immunology, Nov. 2013, vol. Article 402 (Year: 2013).*

* cited by examiner

*Primary Examiner* — Mark V Stevens
*Assistant Examiner* — Alparslan Asan
(74) *Attorney, Agent, or Firm* — Locke Lord LLP; Tim Tingkang Xia, Esq.

(57) ABSTRACT

The present invention discloses a method for maintaining or improving gastrointestinal condition, which includes: administering a lactic acid bacterial composition to a subject in need thereof, wherein the lactic acid bacterial composition comprises: a *Lactobacillus paracasei* ET-66 strain with a deposition number CGMCC 13514. The present invention also discloses a method for maintaining or improving gastrointestinal condition, which includes: administering a lactic acid bacterial fermentation composition to a subject in need thereof, wherein the lactic acid bacterial fermentation composition comprises: a fermentation product of a *Lactobacillus paracasei* ET-66 strain.

11 Claims, 7 Drawing Sheets

USE OF LACTIC ACID BACTERIA OR FERMENTATION PRODUCT THEREOF FOR MAINTAINING OR IMPROVING GASTROINTESTINAL CONDITION

CROSS REFERENCE

This non-provisional application claims priority of Taiwan Invention Patent Application No. 111112005, filed on Mar. 29, 2022, the contents thereof are incorporated by reference herein.

FIELD OF THE INVENTION

The present invention is directed to use of lactic acid bacteria or a fermentation product thereof for medicine and health care, and particularly to use of lactic acid bacteria or a fermentation product thereof for maintaining or improving gastrointestinal condition.

BACKGROUND OF THE INVENTION

*Helicobacter pylori* is one of the major pathogens causing gastritis. With *Helicobacter pylori* infection, chronic gastritis, duodenal ulcer, or gastric ulcer may occur, and the worst is that gastric adenocarcinoma or mucosa-associated lymphoid tissue lymphoma may occur. *Helicobacter pylori* can survive in the gastric environment, which is strongly acidic and contains a trace of oxygen. *Helicobacter pylori* often adheres to the mucosal surface in the form of a cloudy film to neutralize the gastric acid and survive in the low pH environment. The gastric environment also gives *Helicobacter pylori* urea as an essential nutrient and then the urea is hydrolyzed into $NH_3$ and $CO_2$ to elevate the pH in the gastric environment.

The main treatment against *Helicobacter pylori* infection is by the way of triple therapy, where one kind of proton pump inhibitor is used in combination with two kinds of antibiotic. This treatment way may tend to cause a high rate of side effects and low compliance on the patient, and the treatment way may fail because of the bacterial drug resistance and the bacterial infection dose. Accordingly, it begins to look for an alternative way which is mild, safe, and easy. Recently, it is found that certain microorganisms can effectively inhibit *Helicobacter pylori* and improve gastrointestinal health.

Generally, it is safe to take lactic acid bacteria. Therefore, it is a feasible aim to treat *Helicobacter pylori* infection by taking lactic acid bacteria.

SUMMARY OF THE INVENTION

In the present content, it is found that a certain active lactic acid bacterial strain can adhere to gastric cells, inhibit the growth of *Helicobacter pylori* and the activity of urease, and/or agglutinate *Helicobacter pylori*.

In the present content, it is also found that a certain inactivated lactic acid bacterial strain can adhere to gastric cells, inhibit the growth of *Helicobacter pylori* and the activity of urease, and/or agglutinate *Helicobacter pylori*.

In the present content, it is further found that a certain lactic acid bacterial fermentation product can adhere to gastric cells, inhibit the growth of *Helicobacter pylori* and the activity of urease, and/or agglutinate *Helicobacter pylori*.

Based on any of the foregoing findings, the present invention discloses a method for maintaining or improving gastrointestinal condition, which includes: administering a lactic acid bacterial composition to a subject in need thereof, wherein the lactic acid bacterial composition comprises: a *Lactobacillus paracasei* ET-66 strain with a deposition number CGMCC 13514.

In an exemplary embodiment, the lactic acid bacterial composition further comprises: a *Lactobacillus salivarius* subsp. *salicinius* AP-32 strain with a deposition number CCTCC M2011127 and a *Lactobacillus plantarum* LPL28 strain with a deposition number CGMCC 17954.

In an exemplary embodiment, the *Lactobacillus paracasei* ET-66 strain is an active strain or an inactivated strain.

In an exemplary embodiment, the *Lactobacillus salivarius* subsp. *salicinius* AP-32 strain is an active strain or an inactivated strain, and the *Lactobacillus plantarum* LPL28 strain is an active strain or an inactivated strain.

In an exemplary embodiment, the composition is used for adhering to gastric cells, inhibiting *Helicobacter pylori* growth, inhibiting urease activity, and/or agglutinating *Helicobacter pylori*.

Based on any of the foregoing findings, the present invention discloses a method for maintaining or improving gastrointestinal condition, which includes: administering a lactic acid bacterial fermentation composition to a subject in need thereof, wherein the lactic acid bacterial fermentation composition comprises: a fermentation product of a *Lactobacillus paracasei* ET-66 strain.

In an exemplary embodiment, the lactic acid bacterial fermentation composition further comprises: a fermentation product of a *Lactobacillus salivarius* subsp. *salicinius* AP-32 strain and a fermentation product of a *Lactobacillus plantarum* LPL28 strain.

In an exemplary embodiment, the fermentation product of a *Lactobacillus paracasei* ET-66 strain is a fermentation liquid free of bacterial strains, a fermentation liquid containing active bacterial strains, a fermentation liquid containing inactivated bacterial strains, a fermentation liquid containing bacterial lysates, or a powder thereof.

In an exemplary embodiment, the fermentation product of a *Lactobacillus salivarius* subsp. *salicinius* AP-32 strain is a fermentation liquid free of bacterial strains, a fermentation liquid containing active bacterial strains, a fermentation liquid containing inactivated bacterial strains, a fermentation liquid containing bacterial lysates, or a powder thereof, and the fermentation product of a *Lactobacillus plantarum* LPL28 strain is a fermentation liquid free of bacterial strains, a fermentation liquid containing active bacterial strains, a fermentation liquid containing inactivated bacterial strains, a fermentation liquid containing bacterial lysates, or a powder thereof.

In an exemplary embodiment, a bacterial count ratio at fermentation initiation of the *Lactobacillus paracasei* ET-66 strain, the *Lactobacillus salivarius* subsp. *salicinius* AP-32 strain, and the *Lactobacillus plantarum* LPL28 strain is (1 to 8): 1:1.

In an exemplary embodiment, the composition is used for adhering to gastric cells, inhibiting *Helicobacter pylori* growth, inhibiting urease activity, and/or agglutinating *Helicobacter pylori*.

DETAILED DESCRIPTION OF THE INVENTION

The detailed description and preferred embodiments of the invention will be set forth in the following content, and provided for people skilled in the art to understand the characteristics of the invention.

Each bacterial strain used in the present invention is deposited at the China Center for Type Culture Collection in Wuhan University, Wuhan City, China or deposited at the China General Microbiological Culture Collection Center in No. 3, No. 1 Courtyard, Beichen West Road, Chaoyang District, Beijing City, China. Deposition information is listed in Table 1 below.

TABLE 1

Deposition information of lactic acid bacterial strains

| Strain | Accession number | Deposition date |
|---|---|---|
| *Lactobacillus paracasei* ET-66 | CGMCC 13514 | Dec. 29, 2016 |
| *Lactobacillus salivarius* subsp. *salicinius* AP-32 | CCTCC M2011127 | Apr. 10, 2011 |
| *Lactobacillus plantarum* LPL28 | CGMCC 17954 | Jun. 18, 2019 |

An embodiment of the present invention provides a method for maintaining or improving gastrointestinal condition, and the method includes: administering a lactic acid bacterial composition to a subject in need thereof, wherein the lactic acid bacterial composition comprises: a *Lactobacillus paracasei* ET-66 strain. As proven in the following examples, the *Lactobacillus paracasei* ET-66 strain at least can adhere to gastric cells, inhibit *Helicobacter pylori* growth or urease activity, and/or agglutinate *Helicobacter pylori*. Accordingly, the composition can maintain or improve gastrointestinal condition in the subject by way of the foregoing biological function.

In order to enhance the efficiency of maintaining or improving gastrointestinal condition, the composition further comprises: a *Lactobacillus salivarius* subsp. *salicinius* AP-32 strain and a *Lactobacillus plantarum* LPL28 strain. Further, the *Lactobacillus paracasei* ET-66 strain, the *Lactobacillus salivarius* subsp. *salicinius* AP-32 strain, and the *Lactobacillus plantarum* LPL28 strain may be individually an active strain or an inactivated strain. In case of the active strain, the activity of the composition may decrease because of storage or transportation; in case of the inactivated strain, the foregoing problem may not take place.

Another embodiment of the present invention provides a method for maintaining or improving gastrointestinal condition, and the method includes: administering a lactic acid bacterial fermentation composition to a subject in need thereof, wherein the lactic acid bacterial fermentation composition comprises: a fermentation product of a *Lactobacillus paracasei* ET-66 strain. As proven in the following examples, the fermentation product of a *Lactobacillus paracasei* ET-66 strain at least can adhere to gastric cells, inhibit *Helicobacter pylori* growth or urease activity, and/or agglutinate *Helicobacter pylori*. Accordingly, the composition can maintain or improve gastrointestinal condition in the subject by way of the foregoing biological function.

In order to enhance the efficiency of maintaining or improving gastrointestinal condition, the composition further comprises: a fermentation product of a *Lactobacillus salivarius* subsp. *salicinius* AP-32 strain and a fermentation product of a *Lactobacillus plantarum* LPL28 strain. Further, the fermentation product of a *Lactobacillus paracasei* ET-66 strain, the fermentation product of a *Lactobacillus salivarius* subsp. *salicinius* AP-32 strain, and the fermentation product of a *Lactobacillus plantarum* LPL28 strain may individually contain a fermentation liquid free of bacterial strains, a fermentation liquid containing active bacterial strains, a fermentation liquid containing inactivated bacterial strains, a fermentation liquid containing bacterial lysates, or a powder thereof. In case of the fermentation liquid containing active bacterial strains, the activity of the composition may decrease because of storage or transportation; in case of the others, the foregoing problem may not take place.

The fermentation product of a *Lactobacillus paracasei* ET-66 strain, the fermentation product of a *Lactobacillus salivarius* subsp. *salicinius* AP-32 strain, and the fermentation product of a *Lactobacillus plantarum* LPL28 strain may be obtained by way of cultivating the corresponding bacterial strain in a fermentation medium. The fermentation medium may be an MRS broth medium, and the MRS broth medium may contain a carbon source and/or a nitrogen source. An example of the carbon source is glucose, fructose, lactose, sucrose, maltose, galactose, mannose, trehalose, starch, potato starch, malt extract, maltodextrin, or any combination thereof; an example of the nitrogen source is $(NH_4)_2SO_4$, $(NH_4)_3PO_4$, $NH_4NO_3$, $NH_4Cl$, casamino acid, peptone, polypeptone, tryptone, meat extract, yeast extract, milk, skimmed milk powder, soybean flour, whey, or any combination thereof. For example, the fermentation medium contains 1 wt % to 20 wt % of the carbon source and/or 4 wt % to 35 wt % of the nitrogen source. For example, the fermentation medium contains 1 wt % to 5 wt % of glucose, and preferably contains 5 wt % of glucose. For example, the fermentation medium contains 2 wt % to 15 wt % of skimmed milk powder, 3 wt % to 10 wt % of peptone, and/or 1 wt % to 5 wt % of yeast extract, preferably contains 12 wt % of skimmed milk powder, 7 wt % of peptone, and/or 3 wt % of yeast extract.

The term "cultivating" used in this content substantially has the same meaning as the term "incubating", "culturing", and "fermenting", and they are exchangeable with each other. The condition for cultivating can be selected with reference to New Microbiol. 2013 April; 36(2):167-79. For example, the temperature for cultivating is from 25° C. to 40° C., and preferably is 37° C. For example, the period for cultivating is from 6 hours to 12 hours, and preferably is 6 hours.

On condition that the composition includes the fermentation product of a *Lactobacillus paracasei* ET-66 strain, the fermentation product of a *Lactobacillus salivarius* subsp.

salicinius AP-32 strain, and the fermentation product of a *Lactobacillus plantarum* LPL28 strain, all kinds of bacterial strains are mixed to form a bacterial mixture, and then the bacterial mixture is cultivated in a fermentation medium; or, all kinds of bacterial strains are cultivated in a fermentation medium respectively, and then all the fermentation media are mixed. Whichever is adopted, a bacterial count ratio at fermentation initiation of the *Lactobacillus paracasei* ET-66 strain, the *Lactobacillus salivarius* subsp. *salicinius* AP-32 strain, and the *Lactobacillus plantarum* LPL28 strain may be (1 to 8):(1 to 8): 1, and preferably is (1 to 8): 1:1. The phrase "bacterial count ratio at fermentation initiation" is defined as a bacterial count ratio at adding all kinds of bacterial strains to a fermentation medium prior to cultivating (or during cultivating).

Solid-liquid separation may be performed on the cultivated fermentation medium to obtain a supernatant free of bacterial bodies, and the supernatant is a fermentation liquid free of bacterial strains. The "solid-liquid separation" may be defined to include centrifugation, filtration, concentration, or any combination thereof, and preferably is centrifugation.

Drying may be performed on any of the fermentation liquids to form a fermentation powder. For example, drying is performed on the fermentation liquid free of bacterial strains to form a fermentation powder free of bacterial strains, and so forth. The "drying" may be defined to include freeze drying, spray drying, bed drying, or any combination thereof.

The following examples are offered to further illustrate the present invention:

Example 1: Preparation for Fermentation Medium

The fermentation medium used in the following examples is prepared according to the formula listed in Table 2.

TABLE 2

| Formula of fermentation medium | |
| --- | --- |
| Component | Weight percentage (wt %) |
| glucose | 1 to 5 |
| skimmed milk powder | 2 to 15 |
| peptone | 3 to 10 |
| yeast extract | 1 to 5 |
| potassium hydrogen phosphate | 0.05 to 0.2 |
| sodium citrate | 0 to 0.01 |
| manganese (II) sulfate | 0 to 0.01 |
| monosodium glutamate | 1 to 5 |
| Tween 80 | 0.05 to 0.2 |
| water | balance |

Example 2: Options of Bacterial Strains

All lactic acid bacterial strains used in the following examples are listed in

TABLE 3

| Information of bacterial strain | | |
| --- | --- | --- |
| Genus | Strain | Source |
| *Lactobacillus* | *paracasei* LCA506 | purchased from Wei Chuan Foods Corp., Taiwan |
| | *reuteri* DSM 17648 | Purchased from Novozymes A/S, Denmark |

TABLE 3-continued

| Information of bacterial strain | | |
| --- | --- | --- |
| Genus | Strain | Source |
| | *paracasei* ET-66 | isolated from breast milk |
| | *salivarius* subsp. *salicinius* AP-32 | isolated from gastrointestinal tract |
| | *plantarum* LPL28 | isolated from miso |

Example 3: Preparation for Active Strains

A bacterial strain is seeded into a MRS broth medium containing 0.05% of cysteine, and then activated by way of incubation in an incubator with a temperature of 37° C. and a $CO_2$ concentration of 5% for 16 hours. The activated strain is seeded into another MRS broth medium at a concentration of 10 vol %, and then sub-cultured in an incubator with a temperature of 37° C. and a $CO_2$ concentration of 5% for 24 hours. Finally, another fresh MRS broth medium is used to adjust the concentration of the bacterial strain in the medium to $1 \times 10^8$ CFU/mL to $1 \times 10^9$ CFU/mL.

Example 4: Preparation for Inactive Strains

A bacterial strain is activated by way of incubation at a temperature of 37° C. The bacterial strain is inactivated by way of heat-treatment in a 100° C.-water bath for 30 minutes. After centrifugation at a rate of 4,000 rpm for 10 minutes, the supernatant is removed and the remaining precipitate is dissolved in a fresh medium to adjust the concentration of the inactivated bacterial strain in the solution to $5 \times 10^8$ CFU/mL. Centrifugation is performed on the solution to precipitate the inactivated bacterial strain, and spray drying is performed on the precipitated inactivated bacterial strain to form a powder of the inactivated bacterial strain.

Example 5: Preparation for Bacterial Fermentation PRODUCTS

A single kind of bacterial strain is seeded into a 100 mL fermentation medium and then activated by way of incubation at a temperature of 37° C. for 24 hours. Afterward, the activated bacterial strain is seeded into a 5 L fermentation medium at a concentration of 3 vol % (total concentration of the bacterial strain of $5 \times 10^8$ CFU/mL), and then cultivated for fermentation in an anaerobic environment at a temperature of 37° C. overnight. Finally, centrifugation is performed on the fermentation medium to precipitate the bacterial bodies, and spray drying is performed on the supernatant to obtain a fermentation powder of the single kind of bacterial strain.

A single kind of bacterial strain is seeded into a 100 mL fermentation medium and then activated by way of incubation at a temperature of 37° C. for 24 hours. Afterward, multiple kinds of activated bacterial strains are mixed at a certain count ratio. The strain mixture is seeded into a 5 L fermentation medium at a concentration of 3 vol % (total concentration of the bacterial strain of $5 \times 10^8$ CFU/mL), and then cultivated for fermentation in an anaerobic environment at a temperature of 37° C. overnight. Finally, centrifugation is performed on the fermentation medium to precipitate the bacterial bodies, and spray drying is performed on the supernatant to obtain a fermentation powder of the multiple kinds of bacterial strains.

Example 6: Adhesion Analysis to Gastric Cells

This example is performed with reference to Exp Ther Med. 2021 March; 21(3):188. AGS cells are a human gastric adenocarcinoma cell-line and purchased from the American Type Culture Collection.

A sterilized cover glass is positioned in an incubation well. AGS cells are seeded in the well at a density of $3 \times 10^5$ cells/well, and an F12K medium containing 5 µL of 10% of FBS is also added in the well. The cells are incubated in an incubator with a temperature of 37° C. and a $CO_2$ concentration of 5% until the cells approach a 100% confluence. After culture medium substitution, the cells are incubated at a temperature of 37° C. and a $CO_2$ concentration of 5% for 1 hour. After the culture medium is removed and the cells are washed with PBS twice, 1.5 mL of a test sample and 1.5 mL of a fresh culture medium are added into the well and then incubated with the cells in an incubator with a temperature of 37° C. and a $CO_2$ concentration of 5% for 1 to 4 hours. After washing cells with PBS, the cells are fixed with a 10% methanol solution. The cover glass is taken out of the well and Gram staining is performed thereon Finally, the cover glass is observed with an upright microscope and the bacterial count per field on the cover glass is calculated.

Figure 1:
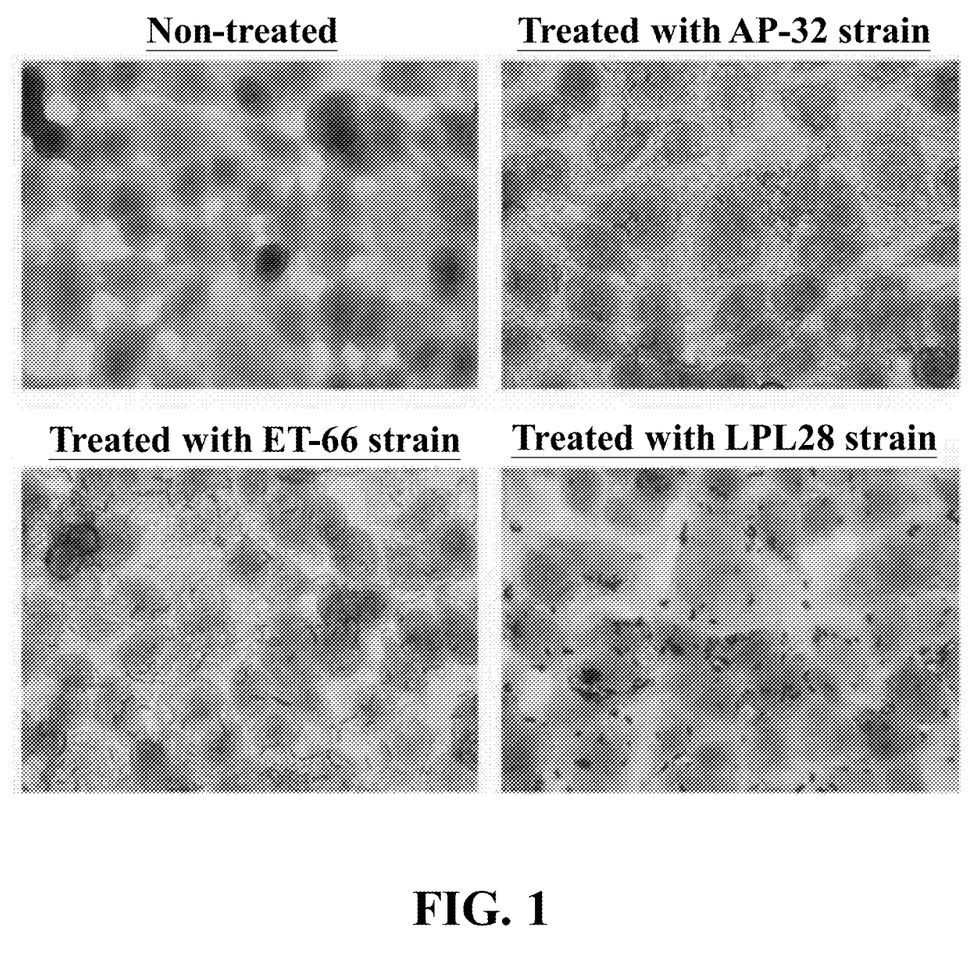
FIG. 1 is a microscopic image showing the adhesion status of different kinds of active lactic acid bacterial strains to gastric cells.
Figure 2:
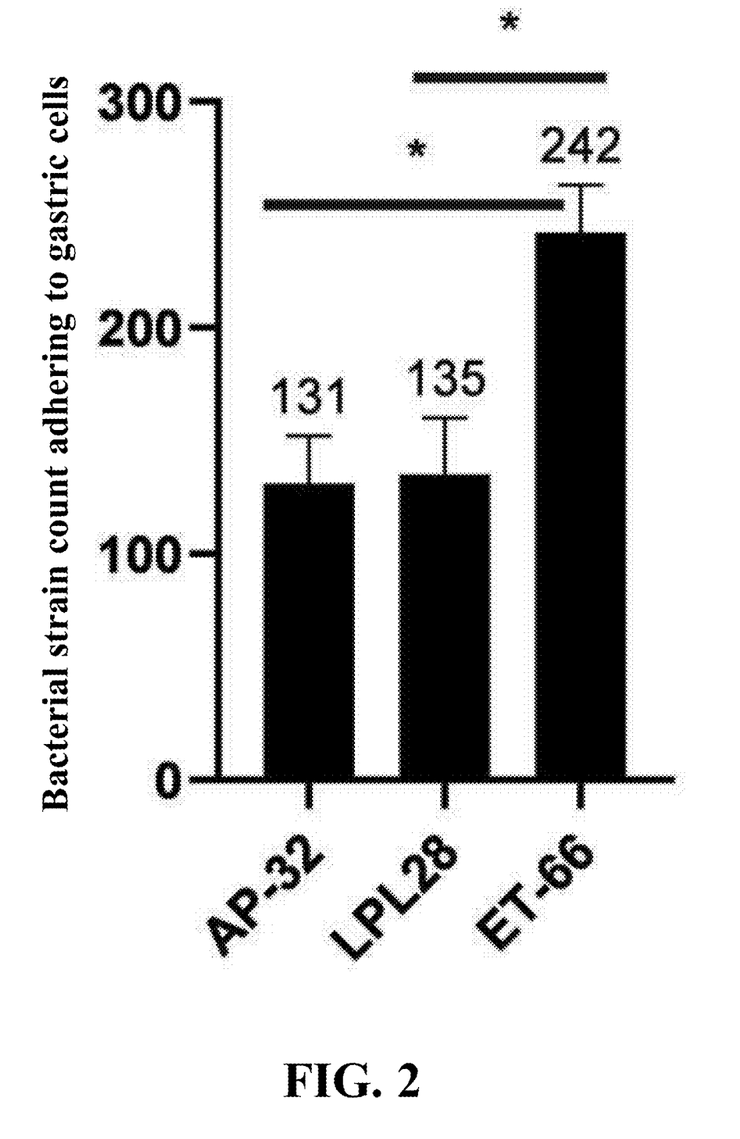
FIG. 2 is a bar graph illustrating the adhesion counts of different kinds of active lactic acid bacterial strains to gastric cells.

As shown in FIGS. 1 to 2, as compared with the active AP-32 strain and the active LPL28 strain, the active ET-66 strain exhibits relatively high activity for adhesion to the gastric cells.

Example 7: Agglutinate Analysis

*Helicobacter pylori* is incubated in a Columbia Broth medium containing 5% of sheep blood for 72 hours. After centrifugation is performed on 1 mL of the bacterial solution at a rate of 4,000 rpm for 10 minutes, the supernatant is removed. *Helicobacter pylori* is washed with 1 mL of PBS, and dissolved in 1 mL of PBS after centrifugation. 1 g of a test sample is taken to be uniformly mixed with 9 mL of PBS. After which, 450 µL of the *Helicobacter pylori* solution dissolved in PBS and 50 µL of the test solution are added into an Eppendorf and mixed with each other for 10 seconds. The mixed solution is placed at a room temperature overnight, and the agglutination status is observed. Specifically, 200 µL of the supernatant is taken to measure the $OD_{600}$ value. The sedimentation rate is calculated following the below formula:

$$\text{Sedimentation rate} = \left(1 - \frac{A}{B}\right) \times 100\%;$$

wherein A indicates the $OD_{600}$ value with adding a powder of an inactivated ET-66 strain or a commercial Pylopass powder, and B indicates the $OD_{600}$ value with adding maltodextrin; the Pylopass powder is a powder of a *Lactobacillus reuteri* DSM 17648 strain purchased from Novozymes A/S, Denmark.

Figure 3:
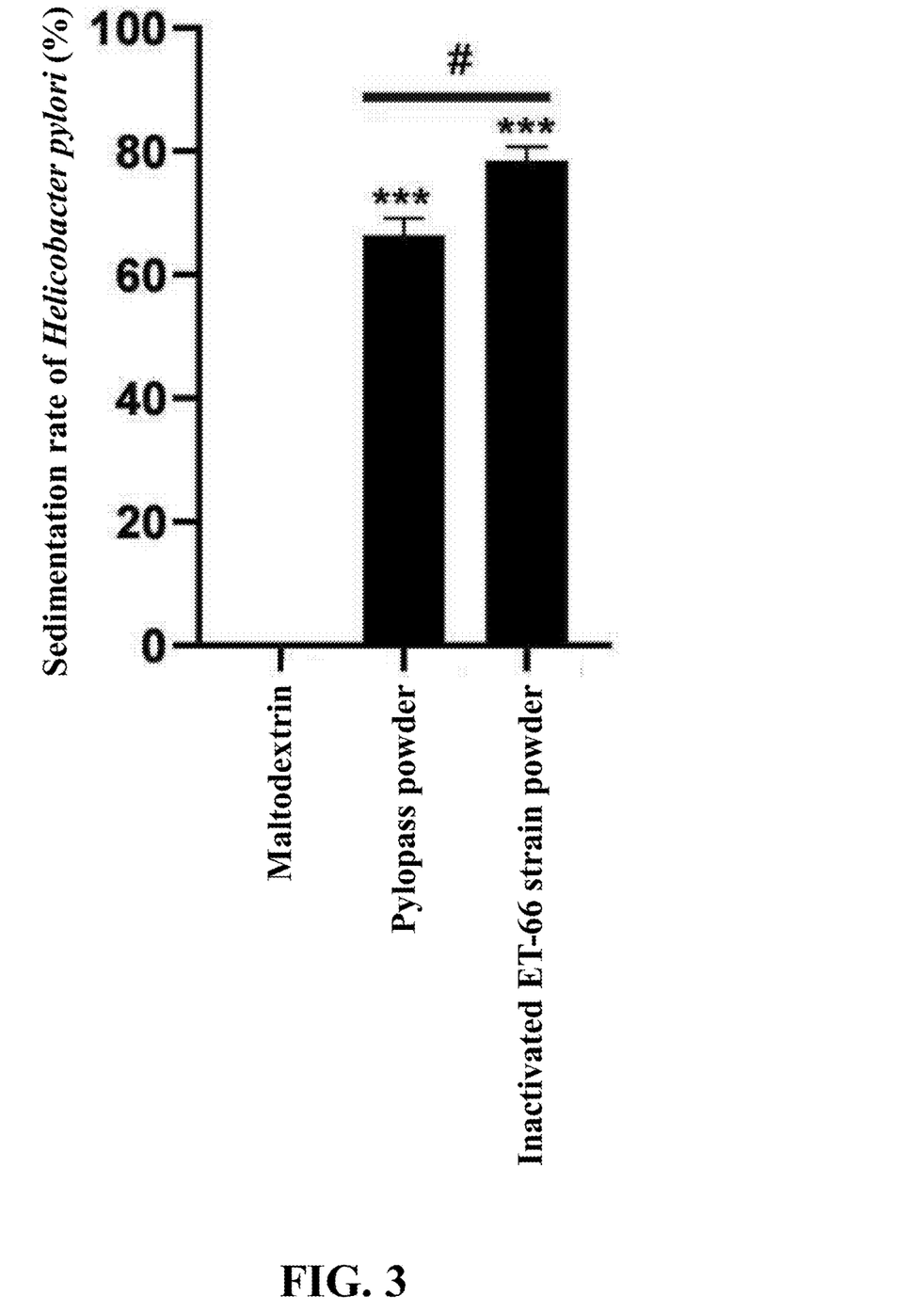
FIG. 3 is a bar graph illustrating the sedimentation rates of *Helicobacter pylori* caused by powders of different kinds of inactivated lactic acid bacterial strains.

As shown in FIG. 3, as compared with the Pylopass powder, the powder of an inactivated ET-66 strain exhibits relatively high activity for agglutinating *Helicobacter pylori*.

Example 8: Analysis for *Helicobacter Pylori* Growth

*Helicobacter pylori* is incubated in a Columbia Broth medium containing 5% of sheep blood for 72 hours. After centrifugation is performed on 1 mL of the bacterial solution at a rate of 4,000 rpm for 10 minutes, the supernatant is removed. *Helicobacter pylori* is dissolved in 1 mL of a Columbia Broth medium containing 5% of sheep, and the *Helicobacter pylori* solution is 10-fold diluted with a fresh Columbia Broth medium. 1 g of a test sample is taken to be uniformly mixed with 9 mL of a Columbia Broth medium. After which, 450 µL of the *Helicobacter pylori* solution and 50 µL of the test solution are mixed and incubated in a microaerophilic environment at a temperature of 37° C. for 72 hours. After 100 µL of the mixed solution is taken for serial dilution, the mixed solution is coated onto a Columbia agar plate. Finally, the Columbia agar plate is placed in a microaerophilic environment at a temperature of 37° C. for 72 hours for incubation, and then the *Helicobacter pylori* count is calculated.

Figure 4:
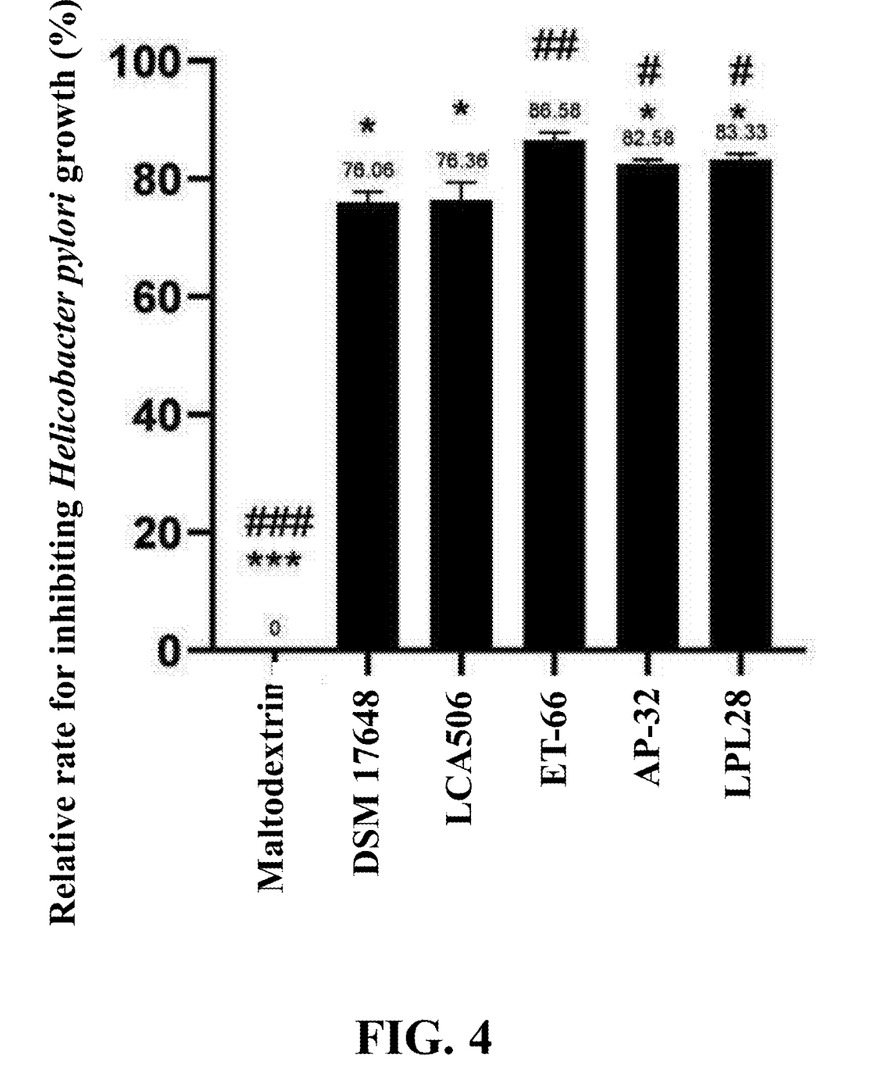
FIG. 4 is a bar graph illustrating the effect of different kinds of active lactic acid bacterial strains on the *Helicobacter pylori* growth.

Firstly, the effect of an active bacterial strain on *Helicobacter pylori* growth is discussed. As shown in FIG. 4, as compared with the active DSM 17648 strain and the active LCA506 strain, the active ET-66 strain, the active AP-32 strain, and the active LPL28 strain all exhibit relatively high activity for inhibiting *Helicobacter pylori* growth.

Figure 5:
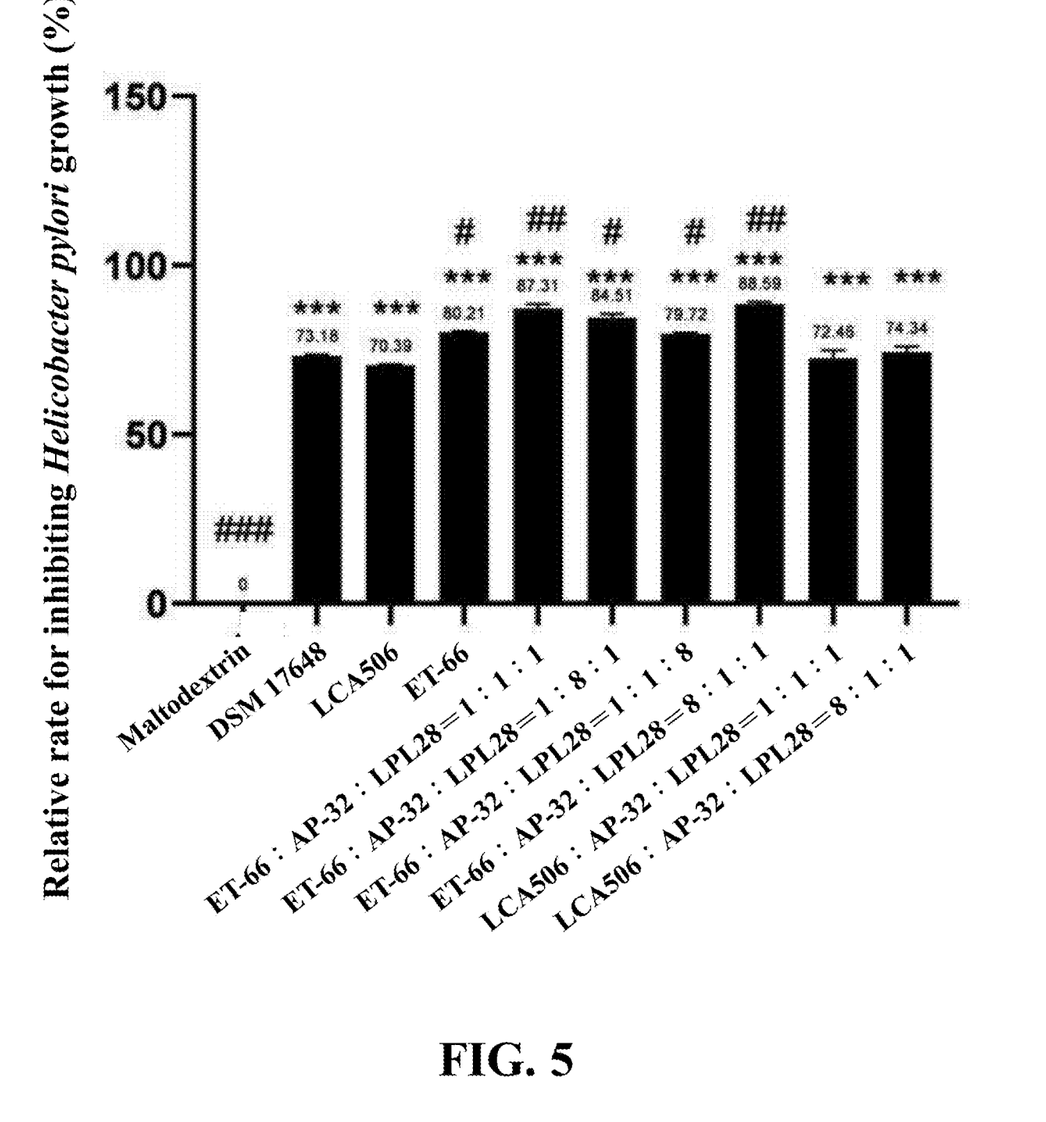
FIG. 5 is a bar graph illustrating the effect of different kinds of lactic acid bacterial fermentation powders on the *Helicobacter pylori* growth.

Secondly, the effect of a bacterial fermentation product on *Helicobacter pylori* growth is discussed. As shown in FIG. 5, as compared with the fermentation powder of a DSM 17648 strain, the fermentation powder of an ET-66 strain and the fermentation powder of a strain mixture containing an ET-66 strain, an AP-32 strain, and an LPL28 strain both exhibit relatively high activity for inhibiting *Helicobacter pylori* growth. With a further discussion, as compared with the fermentation powder of an ET-66 strain, the fermentation powder of a strain mixture exhibits relatively high activity for inhibiting *Helicobacter pylori* growth in case that the bacterial count ratio at fermentation initiation of an ET-66 strain, an AP-32 strain, and an LPL28 strain is (1 to 8):(1 to 8): 1, and particular is (1 to 8): 1:1.

Example 9: Analysis for Urease Activity

*Helicobacter pylori* is incubated in a Columbia Broth medium containing 5% of sheep blood for 72 hours. After centrifugation is performed on 1 mL of the bacterial solution at a rate of 4,000 rpm for 10 minutes, the supernatant is removed. *Helicobacter pylori* is dissolved in 1 mL of a Columbia Broth medium containing 5% of sheep, and the *Helicobacter pylori* solution is 10-fold diluted with a fresh Columbia Broth medium. 1 g of a test sample is taken to be uniformly mixed with 9 mL of a Columbia Broth medium. After which, 450 µL of the *Helicobacter pylori* solution and 50 µL of the test solution are mixed and incubated in a microaerophilic environment at a temperature of 37° C. for 72 hours. After centrifugation is performed on the mixed solution at a rate of 4,000 rpm for 10 minutes, 10 µL of the supernatant is mixed with 300 µL of a urease reaction buffer solution and the reaction mixture is incubated at a temperature of 37° C. for 1.5 hours. Finally, the $OD_{550}$ value of the reaction mixture is measured.

Figure 6:
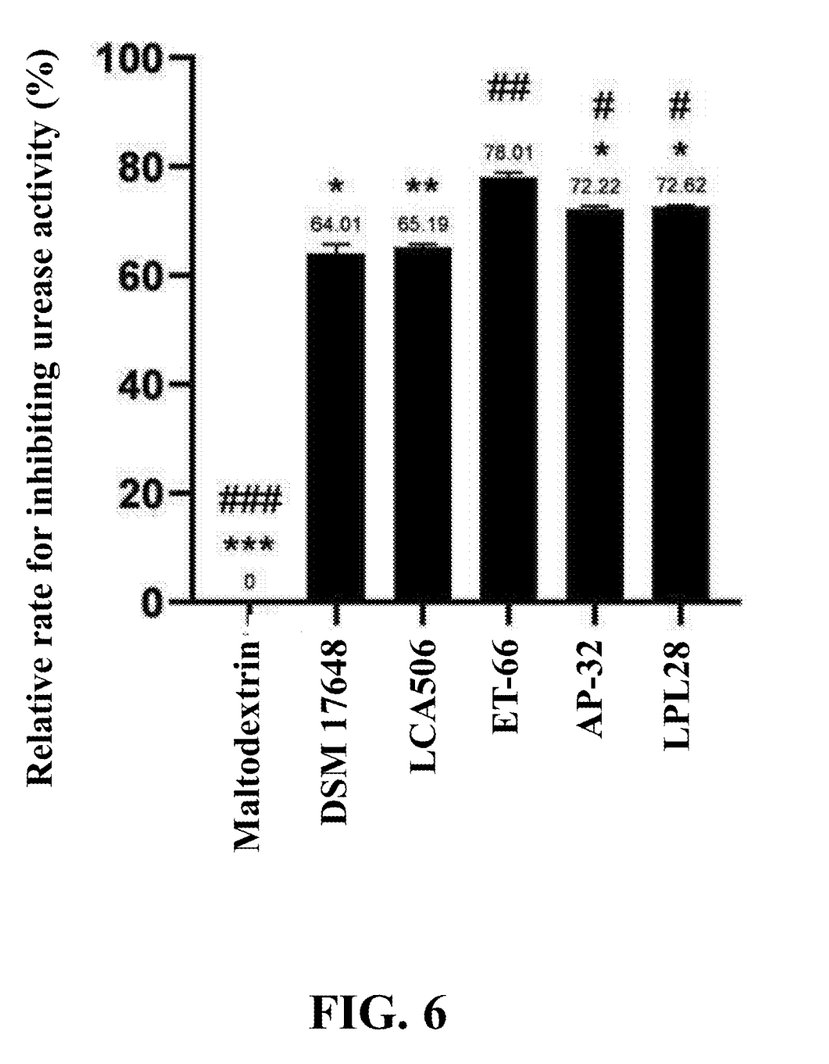
FIG. 6 is a bar graph illustrating the effect of different kinds of active lactic acid bacterial strains on the urease activity.

Firstly, the effect of an active bacterial strain on urease activity is discussed. As shown in FIG. 6, as compared with the active DSM 17648 strain and the active LCA506 strain, the active ET-66 strain, the active AP-32 strain, and the active LPL28 strain all exhibit relatively high activity for inhibiting urease activity.

Figure 7:
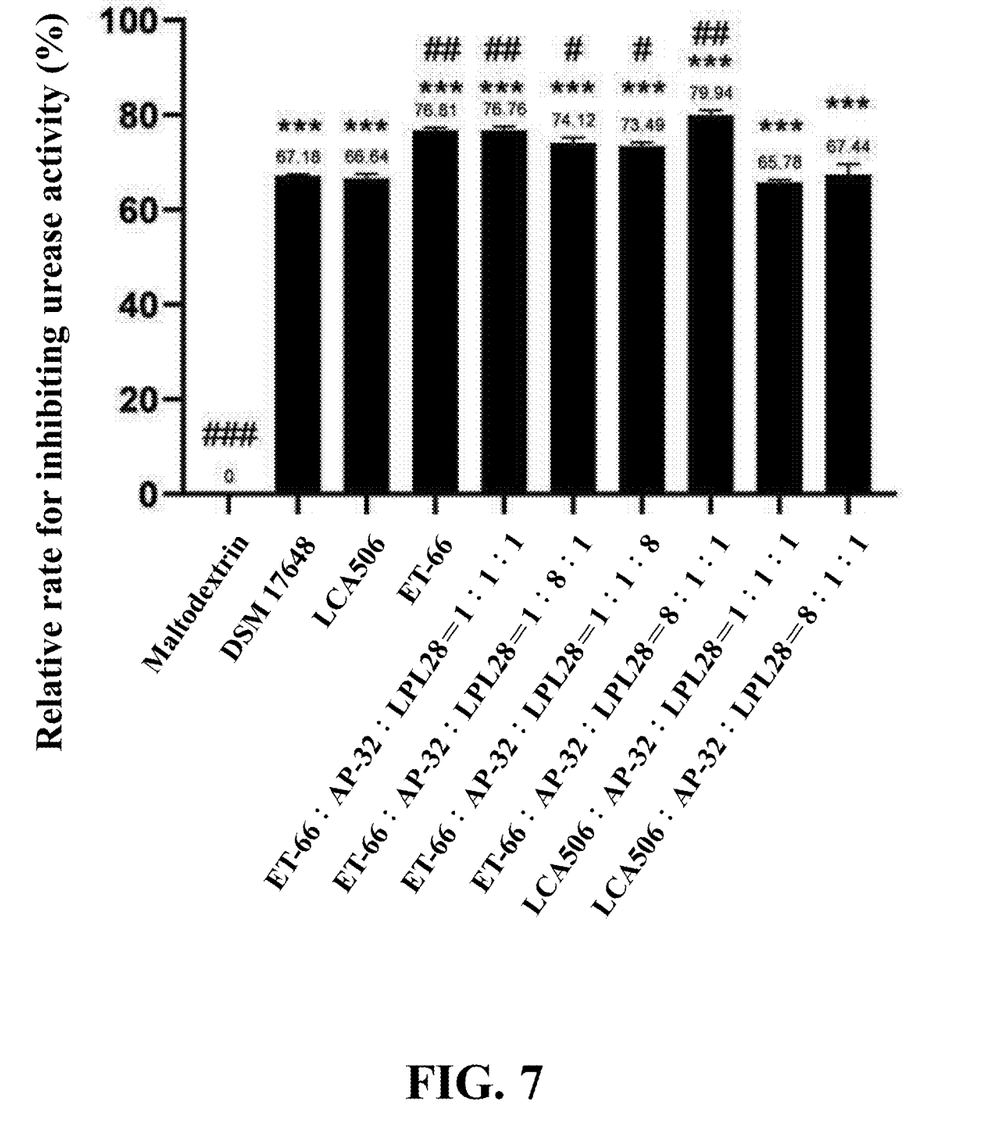
FIG. 7 is a bar graph illustrating the effect of different kinds of lactic acid bacterial fermentation powders on the urease activity.

Secondly, the effect of a bacterial fermentation product on urease activity is discussed. As shown in FIG. 7, as compared with the fermentation powder of a DSM 17648 strain, the fermentation powder of an ET-66 strain and the fermentation powder of a strain mixture containing an ET-66 strain, an AP-32 strain, and an LPL28 strain both exhibit relatively high activity for inhibiting urease activity. With a further discussion, as compared with the fermentation powder of an ET-66 strain, the fermentation powder of a strain mixture exhibits relatively high activity for inhibiting urease activity in case that the bacterial count ratio at fermentation initiation of an ET-66 strain, an AP-32 strain, and an LPL28 strain is 8:1:1.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for treating *Helicobacter pylori* infection, comprising:
   administering a lactic acid bacterial fermentation composition to a subject in need thereof, wherein the lactic acid bacterial fermentation composition consists of: a fermentation product of a *Lactobacillus paracasei* ET-66 strain, a fermentation product of a *Lactobacillus salivarius* subsp. *salicinius* AP-32 strain, and a fermentation product of a *Lactobacillus plantarum* LPL28 strain;
   wherein the *Lactobacillus paracasei* ET-66 strain is deposited at the China General Microbiological Culture Collection Center (CGMCC) with a deposition number CGMCC 13514;
   wherein the *Lactobacillus salivarius* subsp. *salicinius* AP-32 strain is deposited at the China Center for Type Culture Collection (CCTCC) with a deposition number CCTCC M2011127;
   wherein the *Lactobacillus plantarum* LPL28 strain is deposited at the China General Microbiological Culture Collection Center with a deposition number CGMCC 17954;
   wherein the lactic acid bacterial fermentation composition is prepared by mixing the *Lactobacillus paracasei* ET-66 strain, the *Lactobacillus salivarius* subsp. *salicinius* AP-32 strain, and the *Lactobacillus plantarum* LPL28 strain in a fermentation medium at a bacterial count ratio of the *Lactobacillus paracasei* ET-66 strain to the *Lactobacillus salivarius* subsp. *salicinius* AP-32 strain to the *Lactobacillus plantarum* LPL28 strain as (1 to 8):(1 to 8): 1, cultivating the *Lactobacillus paracasei* ET-66 strain, the *Lactobacillus salivarius* subsp. *salicinius* AP-32 strain, and the *Lactobacillus plantarum* LPL28 strain in the fermentation medium, and then performing solid-liquid separation on the fermentation medium;
   wherein the fermentation product of a *Lactobacillus paracasei* ET-66 strain is a fermentation liquid free of bacterial strains or a powder of the fermentation liquid free of bacterial strains, the fermentation product of a *Lactobacillus salivarius* subsp. *salicinius* AP-32 strain is a fermentation liquid free of bacterial strains or a powder of the fermentation liquid free of bacterial strains, and the fermentation product of a *Lactobacillus plantarum* LPL28 strain is a fermentation liquid free of bacterial strains or a powder of the fermentation liquid free of bacterial strains.

2. The method as claimed in claim 1, wherein the fermentation product of a *Lactobacillus paracasei* ET-66 strain is a powder of the fermentation liquid free of bacterial strains, the fermentation product of a *Lactobacillus salivarius* subsp. *salicinius* AP-32 strain is a powder of the fermentation liquid free of bacterial strains, and the fermentation product of a *Lactobacillus plantarum* LPL28 strain is a powder of the fermentation liquid free of bacterial strains.

3. The method as claimed in claim 1, wherein the bacterial count ratio of the *Lactobacillus paracasei* ET-66 strain to the *Lactobacillus salivarius* subsp. *salicinius* AP-32 strain to the *Lactobacillus plantarum* LPL28 strain is 8:1:1.

4. The method as claimed in claim 1, wherein a temperature for the cultivating is from 25 to 40° C.

5. The method as claimed in claim 1, wherein a period for the cultivating is from 6 to 12 hours.

6. The method as claimed in claim 1, wherein a temperature for the cultivating is from 25 to 40° C., and a period for the cultivating is from 6 to 12 hours.

7. The method as claimed in claim 6, wherein the temperature for the cultivating is 37° C., and the period for the cultivating is 6 hours.

8. The method as claimed in claim 1, wherein the bacterial count ratio of the *Lactobacillus paracasei* ET-66 strain to the *Lactobacillus salivarius* subsp. *salicinius* AP-32 strain to the *Lactobacillus plantarum* LPL28 strain is 1:1:1.

9. The method as claimed in claim 1, wherein the bacterial count ratio of the *Lactobacillus paracasei* ET-66 strain to the *Lactobacillus salivarius* subsp. *salicinius* AP-32 strain to the *Lactobacillus plantarum* LPL28 strain is 1:8:1.

10. The method as claimed in claim 1, wherein the solid-liquid separation includes centrifugation or filtration.

11. The method as claimed in claim 1, wherein the fermentation medium comprises: 1 wt % to 5 wt % of glucose, 2 wt % to 15 wt % of skimmed milk powder, 3 wt % to 10 wt % of peptone, 1 wt % to 5 wt % of yeast extract, 0.05 wt % to 0.2 wt % of potassium hydrogen phosphate, 0 wt % to 0.01 wt % of sodium citrate, 0 wt % to 0.01 wt % of manganese (II) sulfate, 1 wt % to 5 wt % of monosodium glutamate, 0.05 wt % to 0.2 wt % of polysorbate 80, and balance wt % of water.

* * * * *